(12) United States Patent
Morimoto

(10) Patent No.: US 10,694,925 B2
(45) Date of Patent: Jun. 30, 2020

(54) ENDOSCOPE

(71) Applicant: FUJIFILM Corporation, Tokyo (JP)

(72) Inventor: Yasuhiko Morimoto, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 214 days.

(21) Appl. No.: 15/298,241

(22) Filed: Oct. 20, 2016

(65) Prior Publication Data

US 2017/0112362 A1    Apr. 27, 2017

(30) Foreign Application Priority Data

Oct. 23, 2015 (JP) ................. 2015-209124

(51) Int. Cl.
*A61B 1/00* (2006.01)
*A61B 1/018* (2006.01)
(Continued)

(52) U.S. Cl.
CPC ...... *A61B 1/00098* (2013.01); *A61B 1/00096* (2013.01); *A61B 1/018* (2013.01);
(Continued)

(58) Field of Classification Search
CPC . A61B 1/00098; A61B 1/00096; A61B 1/018; A61B 1/0669; A61B 8/12; A61B 8/445; A61B 8/461; A61B 8/5207; A61B 1/00163; A61B 1/00174; A61B 1/00177; A61B 1/00179; A61B 1/00181; A61B 1/00183; A61B 1/012; A61B 1/01; A61B 1/0125; A61B 1/0008; A61B 1/00089;
(Continued)

(56) References Cited

U.S. PATENT DOCUMENTS

| 3,404,545 | A | | 10/1968 | Walker | |
|---|---|---|---|---|---|
| 5,562,600 | A | * | 10/1996 | Matsuno | ............ A61B 1/00098 600/107 |

(Continued)

FOREIGN PATENT DOCUMENTS

| CN | 105982636 | 10/2016 |
|---|---|---|
| EP | 1857039 | 11/2007 |

(Continued)

OTHER PUBLICATIONS

"Search Report of Europe Counterpart Application", dated Apr. 3, 2017, p. 1-p. 7, in which the listed references were cited.

(Continued)

*Primary Examiner* — Anh Tuan T Nguyen
*Assistant Examiner* — Pamela F Wu
(74) *Attorney, Agent, or Firm* — JCIPRNET

(57) ABSTRACT

An elevator assembly to be accommodated in the leading end section of the endoscope includes an assembly body, an elevator, and an elevation lever. The elevator includes an elevator rotation shaft portion, the elevation lever includes a lever rotation shaft portion, and the assembly body includes a bearing hole for supporting the rotation shaft portions and. The elevator rotation shaft portion is inserted into the bearing hole from a recessed portion of the assembly body, and the lever rotation shaft portion is inserted into the bearing hole from a side opposite to the recessed portion, and then the shaft portions are coupled to each other.

14 Claims, 11 Drawing Sheets

(51) Int. Cl.
*A61B 1/06* (2006.01)
*A61B 8/12* (2006.01)
*A61B 8/00* (2006.01)

(52) U.S. Cl.
CPC .............. *A61B 1/0669* (2013.01); *A61B 8/12* (2013.01); *A61B 8/445* (2013.01); *A61B 1/0008* (2013.01)

(58) Field of Classification Search
CPC ... A61B 1/00101; A61B 1/00087; A61B 1/04; A61B 1/05; A61B 1/06; A61B 1/0661; A61B 8/52; A61B 1/0676; A61B 1/273; A61B 1/2733; A61B 1/2736; A61B 1/00131; A61B 1/0151; A61M 25/00
USPC ................ 600/127, 129, 104–107, 153, 160, 600/170–176, 113, 109
See application file for complete search history.

(56) References Cited

U.S. PATENT DOCUMENTS

| | | | |
|---|---|---|---|
| 10,165,930 | B2 | 1/2019 | Tanaka et al. |
| 2001/0044570 | A1 | 11/2001 | Ouchi et al. |
| 2004/0082836 | A1 | 4/2004 | Hino |
| 2007/0270638 | A1* | 11/2007 | Kitano ............... A61B 1/00098 600/104 |
| 2018/0092512 | A1* | 4/2018 | Hiraoka ............. A61B 1/00098 |

FOREIGN PATENT DOCUMENTS

| | | |
|---|---|---|
| JP | H114804 | 1/1999 |
| JP | 2002153420 | 5/2002 |
| JP | 2004141315 | 5/2004 |
| JP | 2010201020 | 9/2010 |
| JP | 2014046167 | 3/2014 |
| JP | 2014132923 | 7/2014 |
| JP | 2015058345 | 3/2015 |

OTHER PUBLICATIONS

Office Action of Japan Counterpart Application, with English translation thereof, dated Nov. 19, 2018, pp. 1-8.
"Office Action of China Counterpart Application", dated Aug. 21, 2019, with English translation thereof, p. 1-p. 18.
"Office Action of Japan Related Application No. 2017223475", dated Sep. 10, 2018, with English translation thereof, pp. 1-4.
"Office Action of Related U.S. Appl. No. 15/073,657", dated Oct. 11, 2016, pp. 1-14.
"Office Action of Related U.S. Appl. No. 15/073,657", dated May 1, 2017, pp. 1-13.
"Office Action of Related U.S. Appl. No. 15/073,657", dated Mar. 30, 2018, pp. 1-11.

* cited by examiner

ENDOSCOPE

CROSS-REFERENCE TO RELATED APPLICATIONS

The present application claims priority under 35 U.S.C. § 119 to Japanese Patent Application No. 2015-209124, filed on Oct. 23, 2015. The above application is hereby expressly incorporated by reference, in its entirety, into the present application.

BACKGROUND OF THE INVENTION

Field of the Invention

The present invention relates to an endoscope, and more particularly to an endoscope including an insertion section whose leading end is provided with a treatment tool elevator (hereinafter referred to simply as an elevator) that controls a leading direction of a treatment tool.

Description of the Related Art

In conventional endoscopes, there are known an ultrasound endoscope and a side-viewing endoscope each of which includes a treatment tool leading section through which various treatment tools inserted from a treatment tool inlet provided in an operation section lead out from their leading ends, and an elevator provided in the treatment tool leading section to control a leading direction of a treatment tool.

In addition, there is known an elevator drive mechanism for driving the elevator, the mechanism using an elevation lever coupled to the elevator with a rotation shaft. This allows operation of an operation lever of an operation section to be transferred to the elevation lever through an operation wire so that the elevation lever is turned to turn the elevator, thereby allowing the elevator to rise and lie (refer to Japanese Patent Application Laid-Open No. 2010-201020 and Japanese Patent Application Laid-Open No. 2004-141315).

In the elevator drive mechanism that uses the elevation lever as described above, a seal member is disposed between an outer wall face of the rotation shaft and an internal wall face of a bearing hole in a partition wall, the bearing hole being used for rotatably supporting the rotation shaft. The seal member forms a sealing surface to prevent blood, water, and the like from entering a lever accommodation space for accommodating the elevation lever from an elevator accommodation space for accommodating the elevator.

In the elevator drive mechanism describe above, it is desirable to integrally form the elevator to be disposed in the elevator accommodation space and a portion of the rotation shaft provided closer to the elevator than the seal member, because if blood or the like enters a connection portion therebetween, time and effort is required for cleaning operation.

Unfortunately, if a portion of the rotation shaft to be an elevator side is formed integrally with the elevator, the elevator and the rotation shaft formed integrally with the elevator need to be inserted into the elevator accommodation space and the bearing hole, respectively, at the same time, in assembly operation of the leading end section.

As a result, a width of the elevator accommodation space needs to be sufficiently more than a width of the elevator to cause a problem of an increase in size of the leading end section. Thus, conventionally, the elevator and the rotation shaft are formed separately.

The present invention is made in light of the above-mentioned circumstances, and has an object to provide an endoscope capable of reducing time and effort required for cleaning operation of an elevator without causing a leading end section to increase in size.

SUMMARY OF THE INVENTION

To achieve the object described above, an endoscope in accordance with an aspect of the present invention includes: an insertion section having a leading end and a base end; an operation section provided at the base end of the insertion section; a leading end body provided at the leading end of the insertion section; an elevator that is provided in the leading end body, and has a first rotation shaft portion formed in a direction including a component of a direction orthogonal to a longitudinal axis of the insertion section; an elevation lever that is provided in the leading end body to allow the elevator to rise and lie, the elevator transferring turning force to the first rotation shaft portion; a transfer member that is provided from the operation section to the leading end body through the insertion section to transfer displacement generated in the operation section to the elevation lever; an elevator accommodation section that is provided in the leading end body, and has an elevator accommodation space in which the elevator is accommodated, a partition wall provided between the elevator and the elevation lever, and a bearing hole that is provided in the partition wall to support the first rotation shaft portion; and a seal member provided in the bearing hole. The elevator accommodation space has an open portion opened toward an opposite side to the partition wall in the elevator accommodation section, and the open portion is formed in an area including the elevator disposed in the elevator accommodation space as viewed from an axial direction of the bearing hole. In addition, any posture of the elevator is available when the open portion is defined. More preferably, a posture at a position where the elevator completely rises or lies in an area outside an intraoperative movable range, or in an area within the intraoperative movable range, is available.

According to the present aspect, since the elevator includes the first rotation shaft portion that is rotatably supported in the bearing hole in the elevator accommodation section, a connection portion between members through which blood or the like may enter can be eliminated in a space closer to the elevator than the seal member inside the bearing hole. Thus, cleaning operation is facilitated.

In addition, since the first rotation shaft portion can be inserted into the bearing hole at the same time as the elevator is disposed in the elevator accommodation space from the open portion of the elevator accommodation section, the elevator accommodation space does not need to be increased in width to assemble the elevator in the elevator accommodation section. As a result, the leading end section also does not increase in size.

In another aspect of the present invention, the elevation lever may include a second rotation shaft portion that is coupled to the first rotation shaft portion so that a coupled position between the first rotation shaft portion and the second rotation shaft portion is disposed closer to the elevation lever than the seal member, and a positioning portion that effects positioning of the seal member in the axial direction of the bearing hole.

In yet another aspect of the present invention, the positioning portion may be composed of a position regulation groove provided in the first rotation shaft portion or the second rotation shaft portion.

In yet another aspect of the present invention, the first rotation shaft portion may include: a large diameter portion;

a small diameter portion that is provided adjacent to the large diameter portion on a side facing the elevation lever, and has an outer diameter smaller than that of the large diameter portion; and a first regulation face that is formed in a step between the large diameter portion and the small diameter portion, and has a normal direction that is an axial direction of the first rotation shaft portion, and the second rotation shaft portion may include a second regulation face that faces the first regulation face when coupled to the first rotation shaft portion, and also the positioning portion may be composed of the first regulation face and the second regulation face.

In yet another aspect of the present invention, the positioning portion may be composed of a position regulation groove provided in an internal wall face of the bearing hole of the partition wall.

In yet another aspect of the present invention, the second rotation shaft portion may be coupled to the first rotation shaft portion with a screw.

In yet another aspect of the present invention, the second rotation shaft portion may be coupled to the first rotation shaft portion by fitting.

In yet another aspect of the present invention, the leading end body includes an optical observation section in which an observation window is disposed to acquire an optical image of a subject, and the optical observation section is provided on a side where the open portion of the elevator accommodation section is provided as viewed from the leading end side along the longitudinal axis of the insertion section, and also the optical observation section is provided in an area overlapping with at least the first rotation shaft portion of the elevator as viewed from the axial direction of the bearing hole in a state where the elevator accommodation section and the optical observation section are assembled in the leading end body.

According to the present invention, time and effort required for cleaning operation of the elevator can be reduced without causing the leading end section to increase in size.

DETAILED DESCRIPTION OF THE PREFERRED EMBODIMENTS

Hereinafter, preferable embodiments of the present invention will be described in detail with reference to accompanying drawings.

Figure 1:
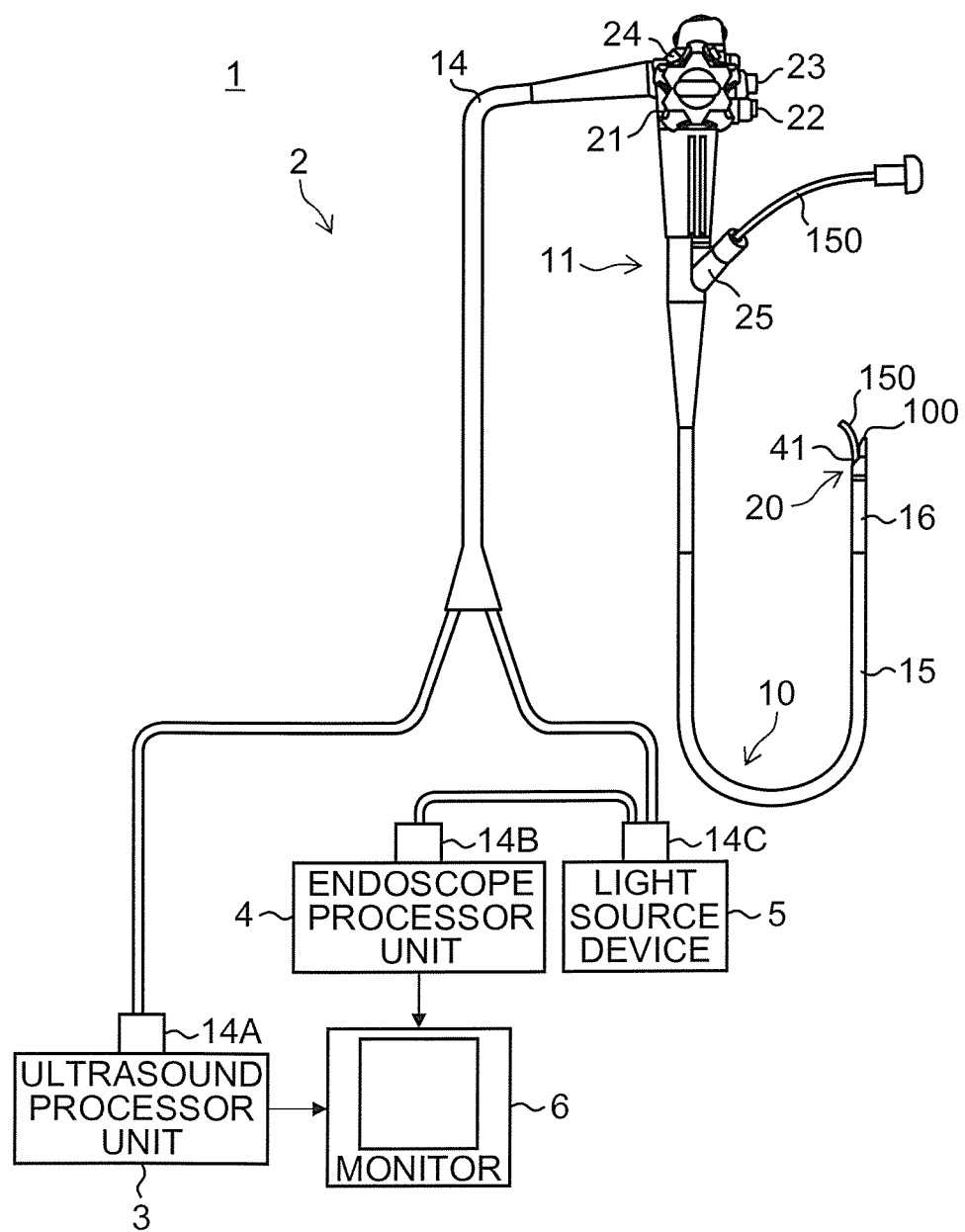
FIG. 1 is a general structural view of an ultrasound inspection system including an ultrasound endoscope to which the present invention is applied.

FIG. 1 is a general structural view of an ultrasound inspection system 1.

The ultrasound inspection system 1 includes an ultrasound endoscope 2 that takes an endoscope image and an ultrasound image in the body, an ultrasound processor unit 3 that generates the ultrasound image, an endoscope processor unit 4 that generates the endoscope image, a light source device 5 that supplies illumination light to the ultrasound endoscope 2 to illuminate the inside of the body, and a monitor 6 that displays the endoscope image and the ultrasound image.

The ultrasound endoscope 2 is a convex type ultrasound endoscope, and includes an insertion section 10 to be inserted into the body, the insertion section 10 having a leading end and a base end, an operation section 11 provided at the base end of the insertion section 10, and a universal cord 14 whose base end is connected to the operation section 11. The universal cord 14 is provided at its leading end with connectors 14A, 14B, and 14C to connect the ultrasound endoscope 2 to the ultrasound processor unit 3, the endoscope processor unit 4, and the light source device 5, respectively.

The insertion section 10 includes a flexible portion 15, a curvature portion 16, and a leading end section 20, which are provided in the order from the base end to the leading end.

The flexible portion 15 has flexibility to curve in any direction along an insertion route of the insertion section 10. The curvature portion 16 curves in each of directions of up and down, and right and left, by operating an angle knob 21 of the operation section 11.

The leading end section 20 is provided at its leading end with an ultrasound observation section 100 that receives and transmits ultrasound, and converts received ultrasound into an ultrasound signal being an electric signal to output the ultrasound signal. The ultrasound signal outputted by the ultrasound observation section 100 is transmitted to the ultrasound processor unit 3 connected through the universal cord 14. Then, the ultrasound processor unit 3 generates a tomographic image, as an ultrasound image, of cellular tissue existing in a depth direction of a body wall portion irradiated with ultrasound.

In addition, the leading end section 20 includes an optical observation section that takes an image of an observed site in the body, and an illumination section that irradiates the observed site with illumination light, each of which is provided at a portion closer to the base end than the ultrasound observation section 100. The image taken by the optical observation section is transmitted to the endoscope processor unit 4 connected through the universal cord 14, as an observation image (endoscope image), and the illumination light emitted by the illumination section is propagated from the light source device 5 connected through the universal cord 14 by passing through a light guide in the ultrasound endoscope 2.

Further, the leading end section 20 includes a treatment tool leading section 41 that is provided at a portion closer to the base end than the ultrasound observation section 100. The treatment tool leading section 41 allows a treatment tool 150 inserted into the treatment tool insertion channel in the insertion section 10 from a treatment tool inlet 25 of the operation section 11 to be led outside the insertion section 10. The treatment tool leading section 41 is provided with an elevator 50 described later to adjust a leading direction of the treatment tool 150.

Figure 2:
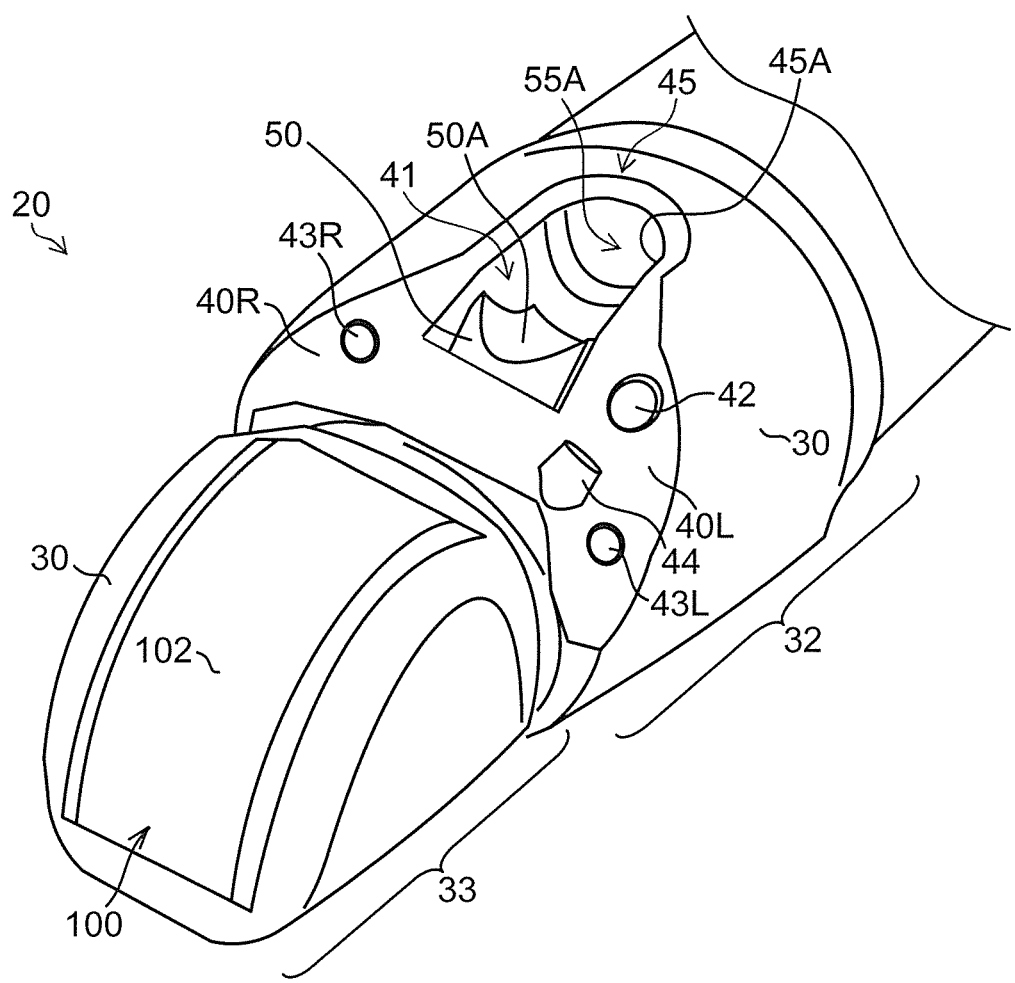
FIG. 2 is a perspective view illustrating a leading end section of the ultrasound endoscope to which the present invention is applied.
Figure 3:
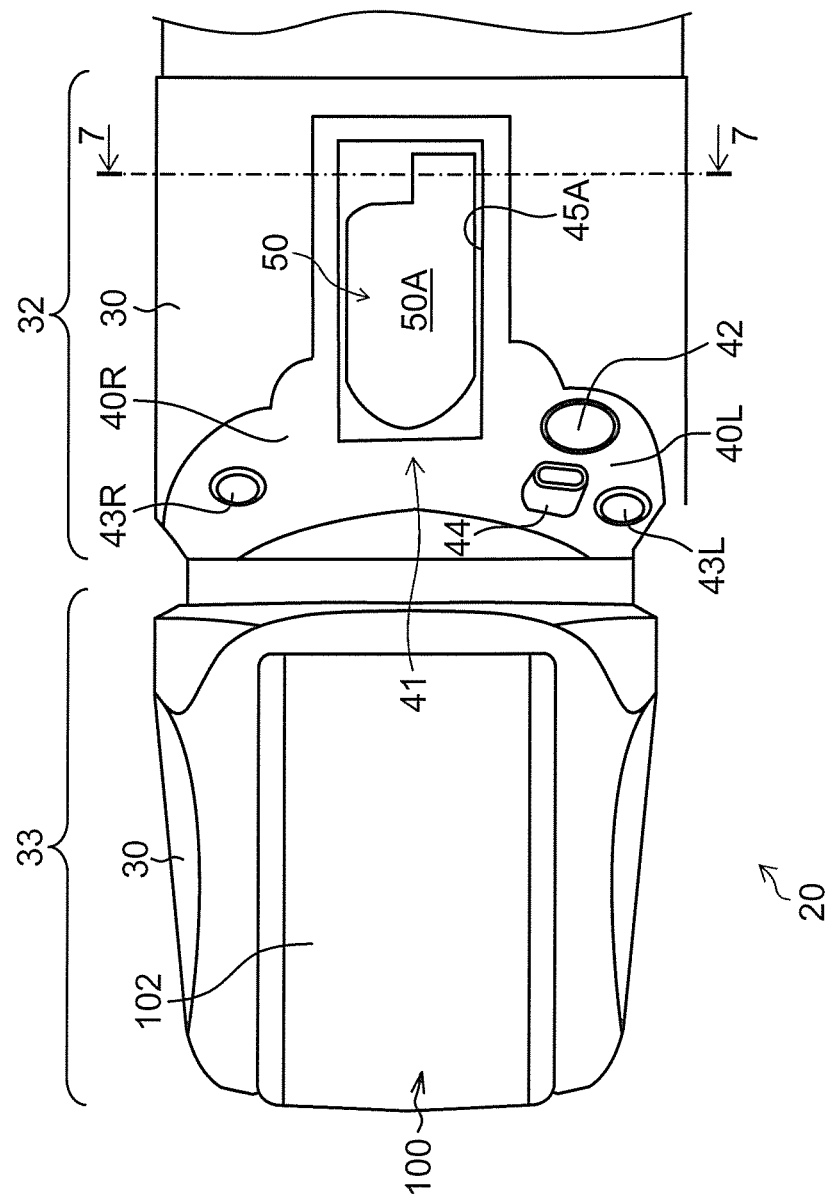
FIG. 3 is a plan view illustrating the leading end section of the ultrasound endoscope to which the present invention is applied.

Next, structure of the leading end section 20 will be described. FIGS. 2 and 3 are a perspective view and a plan view (top view), respectively, illustrating an appearance of the leading end section 20.

The leading end section 20 includes a leading end body 30 that is provided at the leading end of the insertion section 10 to form an outer wall and an inner partition wall of the leading end section 20, a plurality of accommodation sections defined by the leading end body 30, and various components accommodated and held in the accommodation sections.

While detailed description is omitted, a part of the leading end body 30 is detachable as a separate block, and thus each of the components can be assembled in a predetermined accommodation section while the separate block is detached. Attaching the separate block to the leading end body 30 after each of the components is assembled in the corresponding accommodation section allows each of the components to be accommodated and held in the corresponding accommodation section to be fixed to the leading end section 20.

The leading end body 30 is formed of insulating material with insulation, for example, resin material, such as plastic like methacrylate resin and polycarbonate.

The leading end section 20, as illustrated in FIGS. 2 and 3, includes a base section 32 on a base end side, and an extension section 33 extending from the base section 32 to a leading end side.

The extension section 33 is provided with the ultrasound observation section 100 described above on an upper face side of the extension section 33. The ultrasound observation section 100 includes a convex type ultrasound transducer 102 in which a large number of ultrasound vibrators for receiving and transmitting ultrasound are arranged in a convex shape.

When an axial direction of the insertion section 10 is viewed from the base end side of the insertion section 10 to the leading end side thereof, a direction in which the ultrasound observation section 100 and the treatment tool leading section 41 are disposed is referred to as "upper", and a direction opposite to the direction is referred to as "lower", in a direction perpendicular to the axis of the insertion section 10, for terms that indicate up, down, left and right directions.

The base section 32 includes a left inclined face 40L and a right inclined face 40R, extending toward the leading end obliquely upward, and a recessed treatment tool leading section 41 provided in a central portion between the left inclined face 40L and the right inclined face 40R.

The left inclined face 40L includes an observation window 42, an illumination window 43L, and an air-and-water supply nozzle 44. The right inclined face 40R includes an illumination window 43R.

The observation window 42 is provided to acquire an optical image of a subject, and is a component of the optical observation section described above that acquires an image of an observed site as an observation image. In the base section 32 behind the observation window 42, there is accommodated and disposed an imaging system unit that is a component of the optical observation section, and is formed by integrally assembling an imaging optical system and a solid imaging element. The imaging system unit is electrically connected to the endoscope processor unit 4 connected to the universal cord 14.

The illumination windows 43R and 43L each are a component of the illumination section described above that irradiates an observed site with illumination light. In the base section 32 behind the illumination windows 43R and 43L, there is accommodated and disposed a light emission section that is a component of the illumination section, and emits illumination light through the illumination windows 43R and 43L. The light emission section is optically connected to the light source device 5 connected to the universal cord 14, through the light guide.

The air-and-water supply nozzle 44 sprays water and air to the observation window 42 by operating an air-and-water supply button 22 (refer to FIG. 1) of the operation section 11 to perform cleaning of the observation window 42 and the like.

In the treatment tool leading section 41, the elevator 50 is disposed, and an elevator accommodation space 45 having an opening 45A in a side face (upper side) of the leading end body 30 is formed as a slit-like space in which the elevator 50 is disposed, the elevator accommodation space 45 being provided on its base end side with a treatment tool insertion hole 55A.

The treatment tool insertion hole 55A communicates with the treatment tool inlet 25 (refer to FIG. 1) of the operation section 11 through the treatment tool insertion channel (pipe conduit) formed through the inside of the insertion section 10. Thus, the treatment tool inserted from the treatment tool inlet 25 is guided from the treatment tool insertion hole 55A to the elevator accommodation space 45. Then, the elevator 50 in the elevator accommodation space 45 bends a leading direction (leading angle) of the treatment tool so that the treatment tool is led toward a side (upper side) of the insertion section 10 from the treatment tool leading section 41.

The treatment tool insertion channel is also coupled to a suction channel, and body fluid or the like is sucked through the treatment tool insertion hole 55A by operating a suction button 23 (refer to FIG. 1) of the operation section 11.

The elevator 50 includes a guide face 50A that is rotatable provided around a rotation axis in an axial direction including a component of a direction orthogonal to a longitudinal axis of the insertion section 10, and that is a treatment tool guiding face for guiding the treatment tool led from the treatment tool insertion channel. The guide face 50A is formed in a concave shape (arc-like shape) in an upper face of the elevator 50 so as to curve upward from a base end side of the leading end section 20 toward a leading end side thereof.

The treatment tool led to the elevator accommodation space 45 through the treatment tool insertion hole 55A curves upward with respect to an axial direction (longitudinal axis direction of the insertion section 10) of the leading end section 20 along the guide face 50A to be led outside through the opening 45A on an upper side of the elevator accommodation space 45, the opening 45A being a treatment tool outlet.

Since the elevator 50 is configured to rise and lie by operating an elevation operation lever 24 (refer to FIG. 1) of the operation section 11, adjusting an elevation angle from a lying state by allowing the elevator 50 to rise or lie enables adjustment of a leading direction (leading angle) of the treatment tool to be led from the treatment tool leading section 41.

Subsequently, there will be described an elevator assembly 49 that supports and drives the elevator 50 in the leading end section 20.

Figure 4:
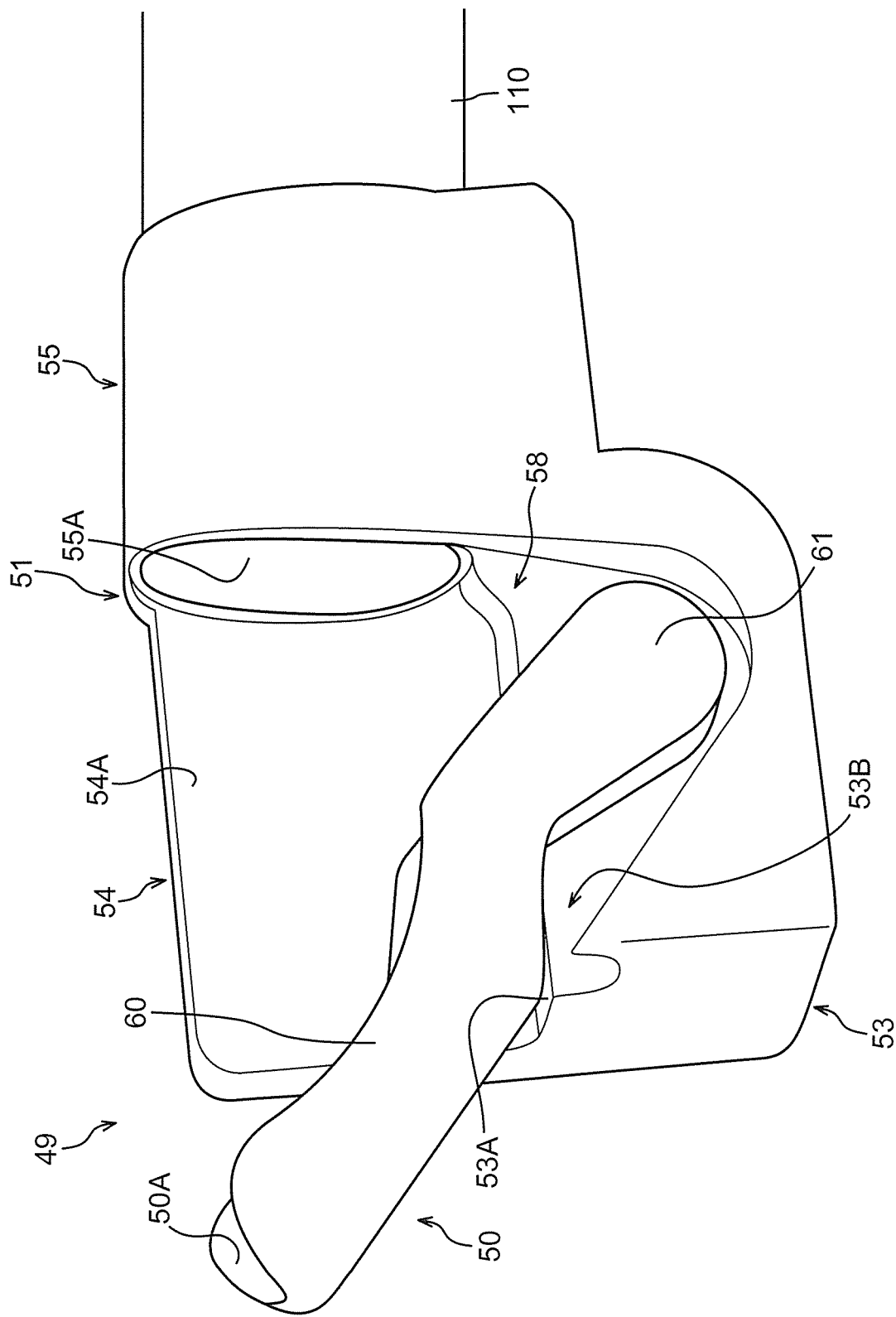
FIG. 4 is a perspective view illustrating the whole of an elevator assembly viewed from the left side.
Figure 5:
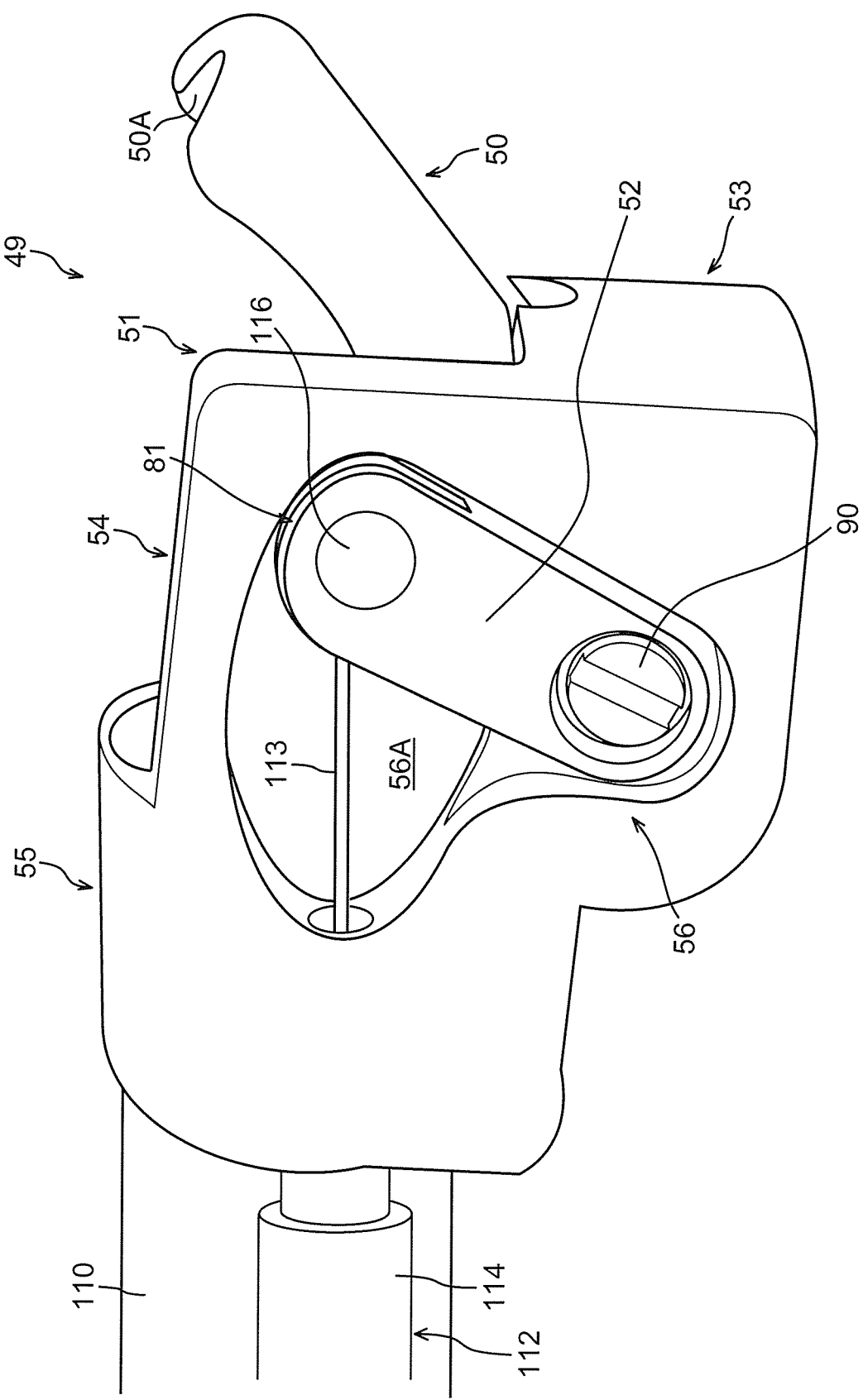
FIG. 5 is a perspective view illustrating the whole of the elevator assembly viewed from the right side.
Figure 6:
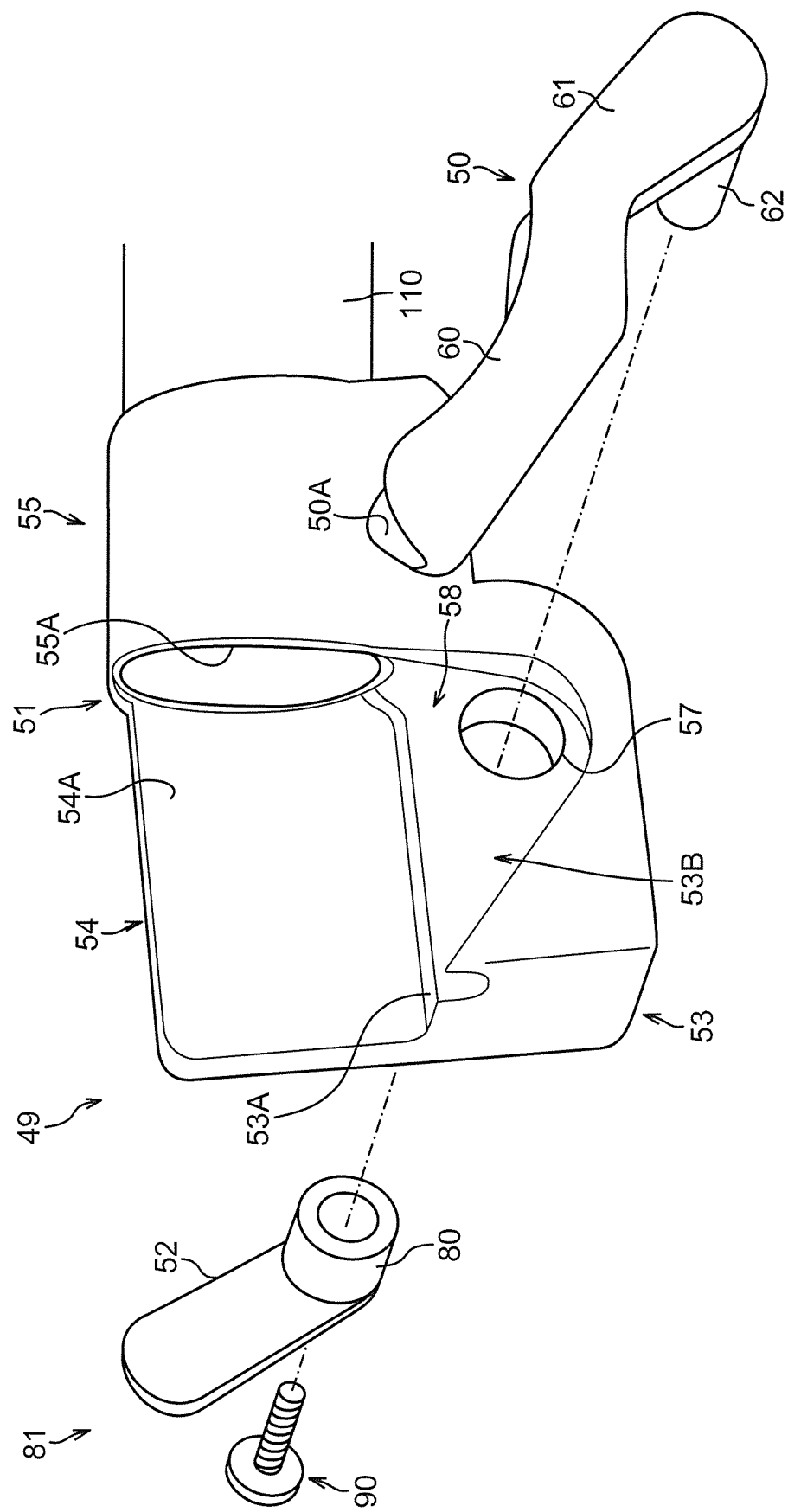
FIG. 6 is an exploded perspective view of the elevator assembly.
Figure 7:
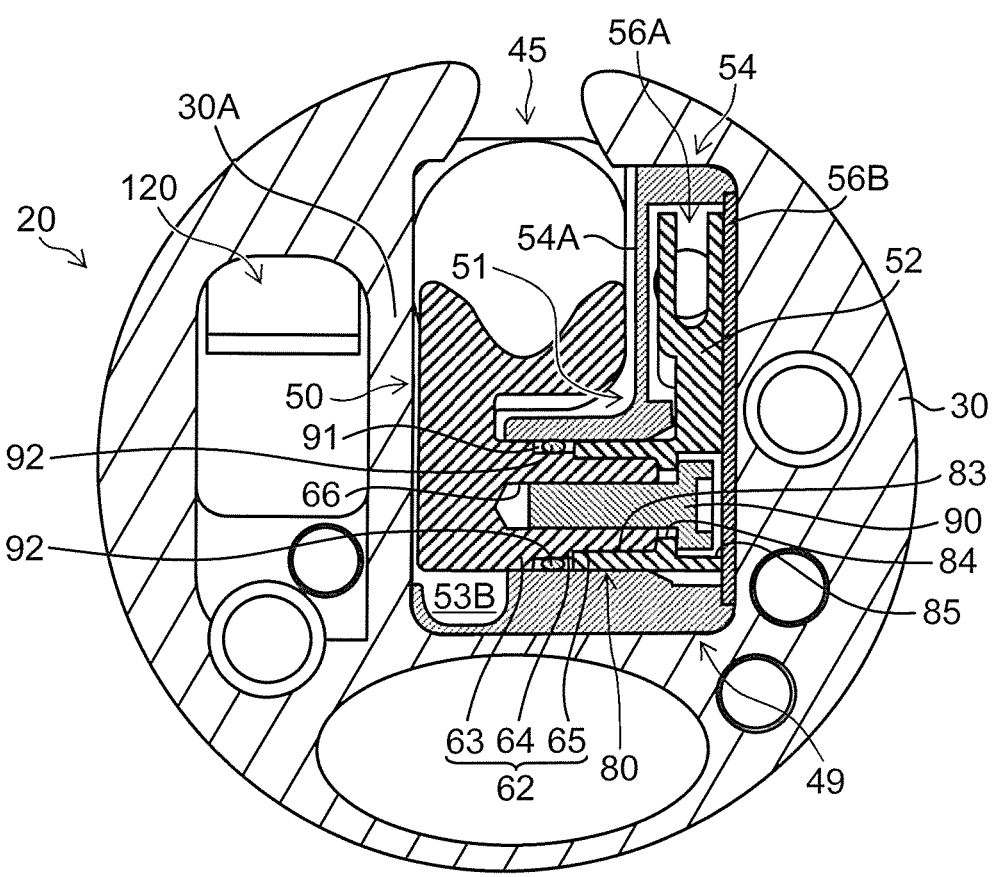
FIG. 7 is a sectional view viewed from a direction of arrows 7-7 in FIG. 3.

FIG. 4 is a perspective view illustrating the elevator assembly 49 viewed from the left side, FIG. 5 is a perspective view illustrating the whole of the elevator assembly 49 viewed from the right side, and FIG. 6 is an exploded perspective view of the elevator assembly 49. FIG. 7 is a sectional view viewed from a direction of arrows 7-7 in FIG. 3.

The elevator assembly 49 is integrally assembled as illustrated in FIGS. 4 and 5, and is accommodated and held in a predetermined accommodation section of the leading end body 30 to be fixed in the leading end section 20 as illustrated in FIG. 7.

As illustrated in FIGS. 4 to 7, the elevator assembly 49 is an elevator accommodation section, and includes an assembly body 51 that supports components, the elevator 50 supported by the assembly body 51, an elevation lever 52 that allows the elevator 50 to rise and lie, and the like. In FIGS. 5 and 6, there is omitted a lid member 56B (refer to FIG. 7) with which a lever accommodation space 56A for accommodating the elevation lever 52 is covered. The elevator accommodation section described above may be the leading end body 30 itself (in this case, the leading end body 30 may be composed of two components), or may be a case disposed in the leading end body 30.

The assembly body 51, as illustrated in FIGS. 4 to 6, includes a base portion 53 that constitutes a lower portion of the assembly body 51, a partition 54 that constitutes an upper right portion of the assembly body 51 and serves as a partition wall between the elevator 50 and the elevation lever 52, along with the base portion 53, and a treatment tool insertion portion 55 that constitutes a base end portion. While these components are integrally formed, separated components may be coupled to each other.

The base portion 53 is disposed below the elevator accommodation space 45 with respect to an area of the elevator accommodation space 45 in a state where the base portion 53 is accommodated in the leading end section 20 (the predetermined accommodation section of the leading end body 30) as the elevator assembly 49 as illustrated in FIGS. 2 and 3 (and FIG. 7).

In an area along a left face of the base portion 53, there is formed a recessed portion 53B for rotatable accommodating a support portion 61 of the elevator 50, the recessed portion 53B having an opened left face.

The partition 54 extends upward at a position along a right edge of a top face 53A of the base portion 53, and a left face 54A of the partition 54 constitutes a right wall face of the elevator accommodation space 45.

The leading end body 30 (a partition wall 30A in FIG. 7) constitutes a left wall face of the elevator accommodation space 45.

A lever accommodation section 56 is provided in an area along the base portion 53 and a right face of the partition 54 (refer to FIG. 5) to constitute the lever accommodation space 56A for rotatable accommodating the elevation lever 52. The lever accommodation space 56A is provided with a cylindrical bearing hole 57 (refer to FIGS. 6 and 7) that penetrates to the recessed portion 53B of the base portion 53 to rotatable support the elevator 50 and the elevation lever 52.

The treatment tool insertion portion 55 is connected to a base end side of each of the base portion 53 and the partition 54, and the treatment tool insertion portion 55 is disposed on a base end side of the elevator accommodation space 45.

The treatment tool insertion portion 55 is provided with the treatment tool insertion hole 55A that opens toward the elevator accommodation space 45. A pipe conduit member 110 constituting the treatment tool insertion channel is connected to a base end side of the treatment tool insertion portion 55 to allow the treatment tool insertion hole 55A to communicate with the treatment tool insertion channel.

The assembly body 51 includes a partition wall between the elevator 50 and the elevation lever 52, the partition wall being composed of the base portion 53 and the partition 54, and the partition wall is provided with the bearing hole 57 for supporting the elevator 50 and the elevation lever 52. The assembly body 51 also includes an open portion 58 opened toward an opposite side to the partition wall with respect to the elevator 50, and the open portion 58 is formed in an area including the elevator 50 as viewed from an axial direction of the bearing hole 57.

In FIG. 7, reference numeral 120 designates the imaging optical system constituting the optical observation section, and in the leading end section 20, the accommodation section for accommodating the elevator assembly 49 and an accommodation section for accommodating an imaging-system assembly in which components of the optical observation section are integrally assembled are separated by the partition wall 30A being a part of the leading end body 30. That is, when viewed from the leading end side along the longitudinal axis of the insertion section 10, the optical observation section is provided on a side where the open portion 58 of the elevator assembly 49 is provided. In a state where the elevator assembly 49 and the optical observation section are assembled in the leading end body 30, the optical observation section is provided in an area overlapping with at least an elevator rotation shaft portion 62 (described later) of the elevator 50 as viewed from an axial direction of the bearing hole 57.

The elevator 50 includes the elevator body 60 with a bilaterally symmetrical shape that is provided with the arc-like guide face 50A as described above, the support portion 61 that extends downward from a base end portion of the elevator body 60 and has a lateral width less than that of the elevator body 60, and the elevator rotation shaft portion 62 that is formed to project from the support portion 61 in a direction including a component of a direction orthogonal to the longitudinal axis of the insertion section 10, the elevator rotation shaft portion 62 being formed as a first rotation shaft portion.

The elevator rotation shaft portion 62 is inserted into the bearing hole 57 of the assembly body 51 from a recessed portion 53B side, and is rotatable supported in the bearing hole 57.

Accordingly, the support portion 61 of the elevator 50 is accommodated in the recessed portion 53B to be rotatable around an axis of the elevator rotation shaft portion 62, or around an axis of the bearing hole 57.

The elevator body 60 is accommodated at a position facing the treatment tool insertion hole 55A of the elevator accommodation space 45 to be rotatable around the axis of the bearing hole 57, or to be able to rise and lie.

The elevation lever 52 is formed in the shape of an elongated plate, and includes a lever rotation shaft portion 80 as a second rotation shaft portion that projects from one end side (base end side) of the elevation lever 52 in a longitudinal direction. At the other end (leading end side), a wire coupling portion 81 to which an operation wire 113 is to be coupled is formed.

The lever rotation shaft portion 80 is inserted into the bearing hole 57 of the assembly body 51 from the lever accommodation space 56A side to be coupled to the elevator rotation shaft portion 62 of the elevator 50, and is fixed to the elevator rotation shaft portion 62 with a screw 90.

Accordingly, the lever rotation shaft portion 80 is formed coaxially with the elevator rotation shaft portion 62 to be coupled to the elevator rotation shaft portion 62, and thus the lever rotation shaft portion 80 is rotatably supported in the bearing hole 57 to be rotated integrally with the elevator rotation shaft portion 62. Details of a coupling mechanism of the elevator rotation shaft portion 62 and the lever rotation shaft portion 80 will be described later.

The elevation lever 52 is accommodated in the lever accommodation space 56A to be rotatable around an axis of the lever rotation shaft portion 80, or around the axis of the bearing hole 57.

Meanwhile, as illustrated in FIG. 5, a control cable 112 including a guide tube 114 and the operation wire 113 inserted into the guide tube 114 is connected to a base end side of the lever accommodation section 56 in a base end portion of the treatment tool insertion portion 55 of the assembly body 51. One end (base end) of the operation wire 113 is coupled to the elevation operation lever 24 of the operation section 11, and the operation wire 113 is pushed and pulled by operating the elevation operation lever 24. The other end (leading end) of the operation wire 113 is inserted into the lever accommodation space 56A to be coupled to the wire coupling portion 81 of the elevation lever 52 through a connection member 116.

According to the elevator assembly 49 described above, when the operation wire 113 is pushed or pulled by operating the elevation operation lever 24, the elevation lever 52 turns around the axis of the lever rotation shaft portion 80. Then, the elevator rotation shaft portion 62 turns in conjunction with turning of the elevation lever 52 so that the elevator 50 rises and lies.

While an aspect of a transfer member for transferring displacement generated by the operation section 11 to the elevation lever 52 is the operation wire 113 that is provided from the operation section 11 to the leading end body 30 through the insertion section 10, another aspect is available.

Subsequently, a coupling mechanism for coupling the elevator 50 and the elevation lever 52 to each other (hereinafter, referred to as an elevator-lever coupling mechanism) will be described.

Figure 8:
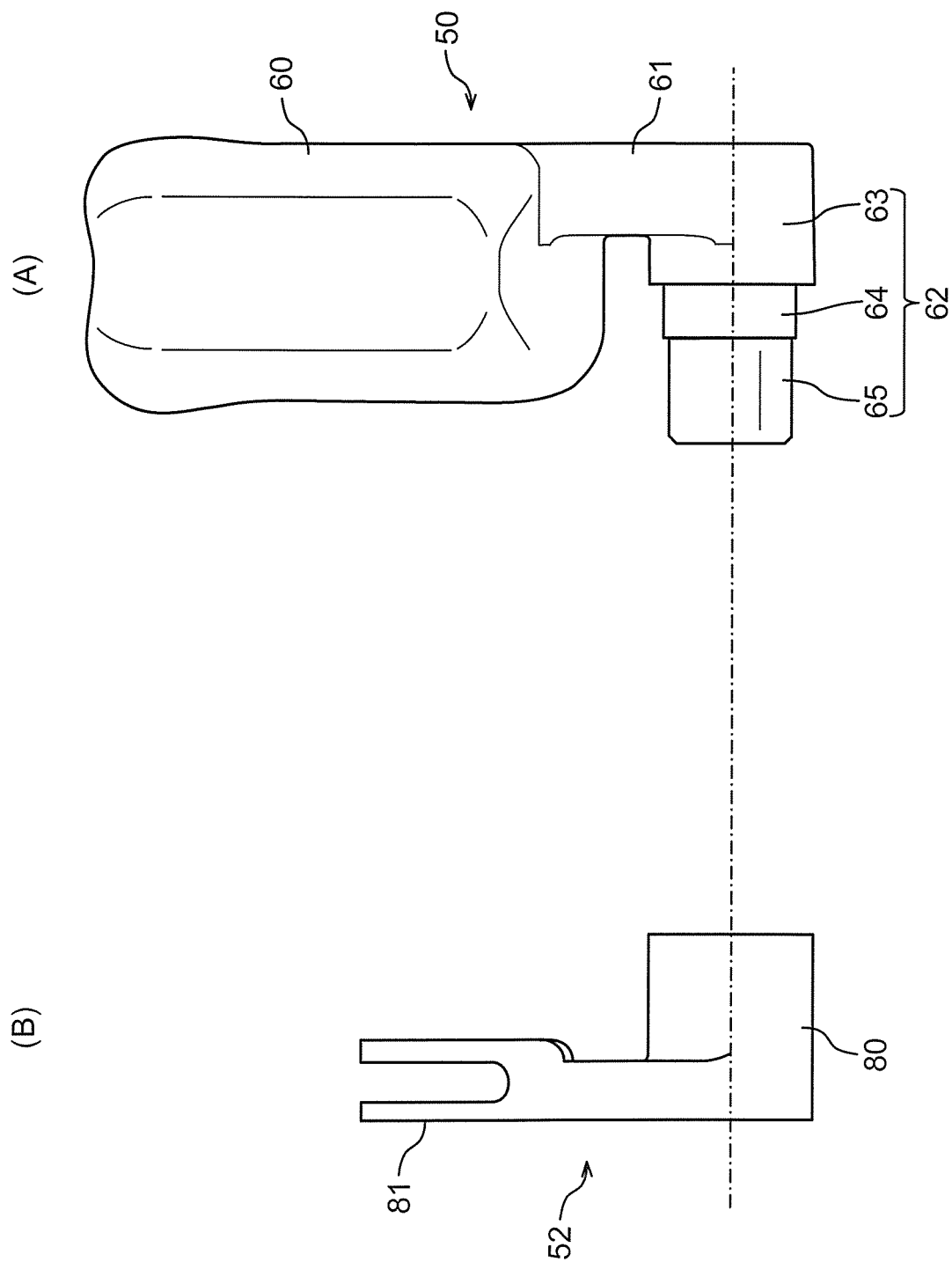
FIG. 8 is a front view of an elevator and an elevation lever of a first embodiment in a coupling mechanism of a first embodiment for coupling the elevator and the elevation lever.
Figure 9:
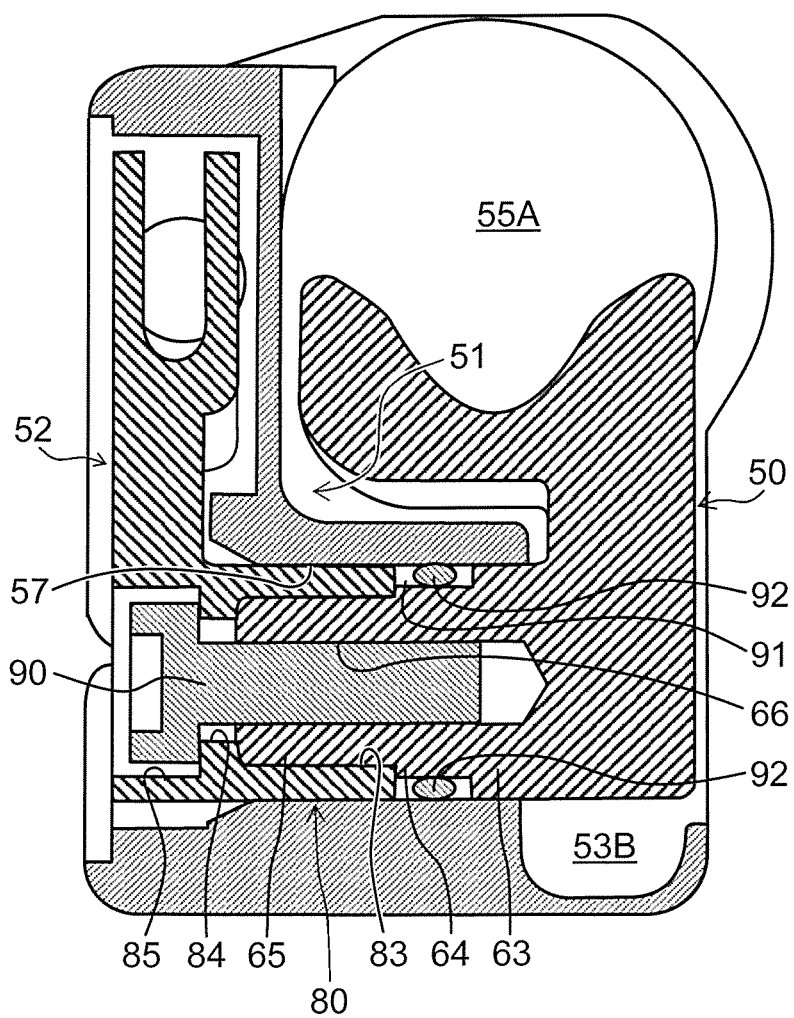
FIG. 9 is a sectional view of the coupling mechanism of the first embodiment in the elevator assembly, taken along a plane including an axis of an elevator rotation shaft portion, the plane being perpendicular to an axis of an insertion section.

FIG. 8 is a front view of the elevator 50 and the elevation lever 52 of the first embodiment in the elevator-lever coupling mechanism of the first embodiment, and FIG. 9 is a sectional view of the elevator-lever coupling mechanism of the first embodiment in the elevator assembly 49, taken along a plane including the axis of the elevator rotation shaft portion 62 (bearing hole 57), the plane being perpendicular to an axis of the leading end section 20 (longitudinal axis of the insertion section 10).

As illustrated in the (A) portion of FIGS. 8 and 9, the elevator rotation shaft portion 62 of the elevator 50 projects from the support portion 61, and includes a large diameter portion 63, a small diameter portion 64, and a rotation regulation portion 65 in order from the support portion 61.

The large diameter portion 63 is formed like a column, and has an outer diameter that is substantially equal to an inner diameter of the bearing hole 57 of the assembly body 51.

The small diameter portion 64 is provided adjacent to the large diameter portion 63 on a side facing the elevation lever 52, and is formed like a column. In addition, the small diameter portion 64 has an outer diameter smaller than the outer diameter of the large diameter portion 63, and is provided with a seal member 92 (refer to FIG. 9) that is fit around the small diameter portion 64.

The rotation regulation portion 65 extends from the small diameter portion 64, and is formed like a quadrangular prism. In addition, the rotation regulation portion 65 like a quadrangular prism has a diagonal length (diameter of a circumscribed cylinder) smaller than the outer diameter of the small diameter portion 64.

In addition, a screw hole 66 (refer to FIG. 9) is formed from a leading end face of the rotation regulation portion 65 toward an opposite face thereof, along an axis of the elevator rotation shaft portion 62.

Meanwhile, as illustrated in the (B) portion of FIGS. 8 and 9, the lever rotation shaft portion 80 of the elevation lever 52 is formed like a column, and has an outer diameter that is substantially equal to the inner diameter of the bearing hole 57 of the assembly body 51.

A fitting hole 83 like a quadrangular prism is formed in a leading end face of the lever rotation shaft portion 80 toward an opposite face thereof along the axis of the lever rotation shaft portion 80 so that the rotation regulation portion 65 of the elevator rotation shaft portion 62 can be fitted into the fitting hole 83 substantially without a gap.

The fitting hole 83 has an axial length that is substantially equal to an axial length of the rotation regulation portion 65.

In addition, a screw insertion hole 84 having a diameter smaller than a diagonal length of the fitting hole 83 is formed in a bottom face of the fitting hole 83 toward a face opposite to the bottom face, along the axis of the lever rotation shaft portion 80. Then, a counterbore hole 85 having an inner diameter larger than an inner diameter of the screw insertion hole 84 is formed while communicating with the screw insertion hole 84, and penetrates to a face opposite to the leading end face of the lever rotation shaft portion 80.

The elevator 50 and the elevation lever 52 in the elevator-lever coupling mechanism of a first embodiment described above allow the elevator rotation shaft portion 62 of the elevator 50 to be inserted from the recessed portion 53B in the assembly body 51 of the elevator assembly 49, and allow the lever rotation shaft portion 80 of the elevation lever 52 to be inserted into the bearing hole 57 from the lever accommodation space 56A opposite to the recessed portion 53B.

The rotation regulation portion 65 of the elevator rotation shaft portion 62 is fitted into the fitting hole 83 of the lever rotation shaft portion 80, and the elevator rotation shaft portion 62 and the lever rotation shaft portion 80 are coupled to each other at a predetermined rotation angle. Then, the screw 90 with a head part is inserted into the counterbore hole 85 of the elevation lever 52 to be screwed into the screw hole 66 of the elevator rotation shaft portion 62.

As a result, the elevator rotation shaft portion 62 and the lever rotation shaft portion 80 are coupled to each other.

In a state where the elevator rotation shaft portion 62 and the lever rotation shaft portion 80 are coupled to each other as described above, the elevator rotation shaft portion 62 and the lever rotation shaft portion 80 are fixed while the leading end face of the lever rotation shaft portion 80 is in contact with a stepped face formed in a step between the small diameter portion 64 and the rotation regulation portion 65 of the elevator rotation shaft portion 62. Then, a seal groove 91 along a circumferential direction, as a position regulation groove of the seal member 92, is formed between a first regulation face that is a stepped face formed in a step between the large diameter portion 63 and the small diameter portion 64 of the elevator rotation shaft portion 62, and a second regulation face that is the leading end face of the lever rotation shaft portion 80 and faces the first regulation face. The first regulation face and the second regulation face each have a normal direction that is an axial direction of the elevator rotation shaft portion 62.

Meanwhile, before the elevator rotation shaft portion 62 is inserted into the bearing hole 57 of the assembly body 51, the seal member 92 such as an O-ring is fitted around an outer peripheral surface of the small diameter portion 64. Thus, when the elevator rotation shaft portion 62 is inserted into the bearing hole 57 to couple the elevator rotation shaft portion 62 and the lever rotation shaft portion 80 to each other, the seal groove 91 serves as a positioning portion for positioning the seal member 92 in the axial direction of the bearing hole 57 to allow the seal member 92 to be disposed in the seal groove 91 while the seal member 92 is positioned. Then, the seal member 92 is brought into close contact with an internal wall face of the bearing hole 57.

Accordingly, the lever accommodation space 56A of the lever accommodation section 56 is airtightly sealed from the elevator accommodation space 45 to prevent blood, water, and the like, from entering the lever accommodation space 56A from the elevator accommodation space 45.

In addition, since a coupled position of the elevator rotation shaft portion 62 and the lever rotation shaft portion 80 is positioned closer to the elevation lever 52 than the seal member 92, blood, water, or the like cannot enter the lever accommodation space 56A from the elevator accommodation space 45 through a gap in a coupling portion of the elevator rotation shaft portion 62 and the lever rotation shaft portion 80. Further, there is no coupling portion between members through which blood, water, or the like enters, in a portion closer to the elevator accommodation space 45 than the seal member 92.

The elevator accommodation space 45 has the open portion 58 on a side opposite to the partition wall of the assembly body 51 with respect to the elevator 50, and thus when the elevator assembly 49 is assembled, the elevator 50 can be inserted into the elevator accommodation space 45 from the open portion 58 to be disposed, and the elevator rotation shaft portion 62 can be inserted into the bearing hole 57 from the open portion 58 to be disposed. Thus, no extra space is needed to dispose the elevator 50 in the elevator accommodation space 45, and a width of the elevator accommodation space 45 can be substantially equal to a width of the elevator body 60, whereby the leading end section 20 is prevented from increasing in size.

Instead of the seal groove 91 of the present embodiment, as the seal groove for disposing the seal member 92, for example, a groove in a circumferential direction may be formed in the elevator rotation shaft portion 62 or the lever rotation shaft portion 80, or a groove in a circumferential direction is formed in the internal wall face of the bearing hole 57, and the groove may serve as a seal groove (position regulation groove).

Unfortunately, since it is not easy to form a groove in the circumferential direction in the elevator rotation shaft portion 62 formed integrally with the elevator body 60 and the like, or in the bearing hole 57, forming the seal groove 91 by combination with lever rotation shaft portion 80 like the present embodiment enables the elevator 50 and the like to be easily worked.

Next, a second embodiment of the elevator-lever coupling mechanism will be described.

Figure 10:
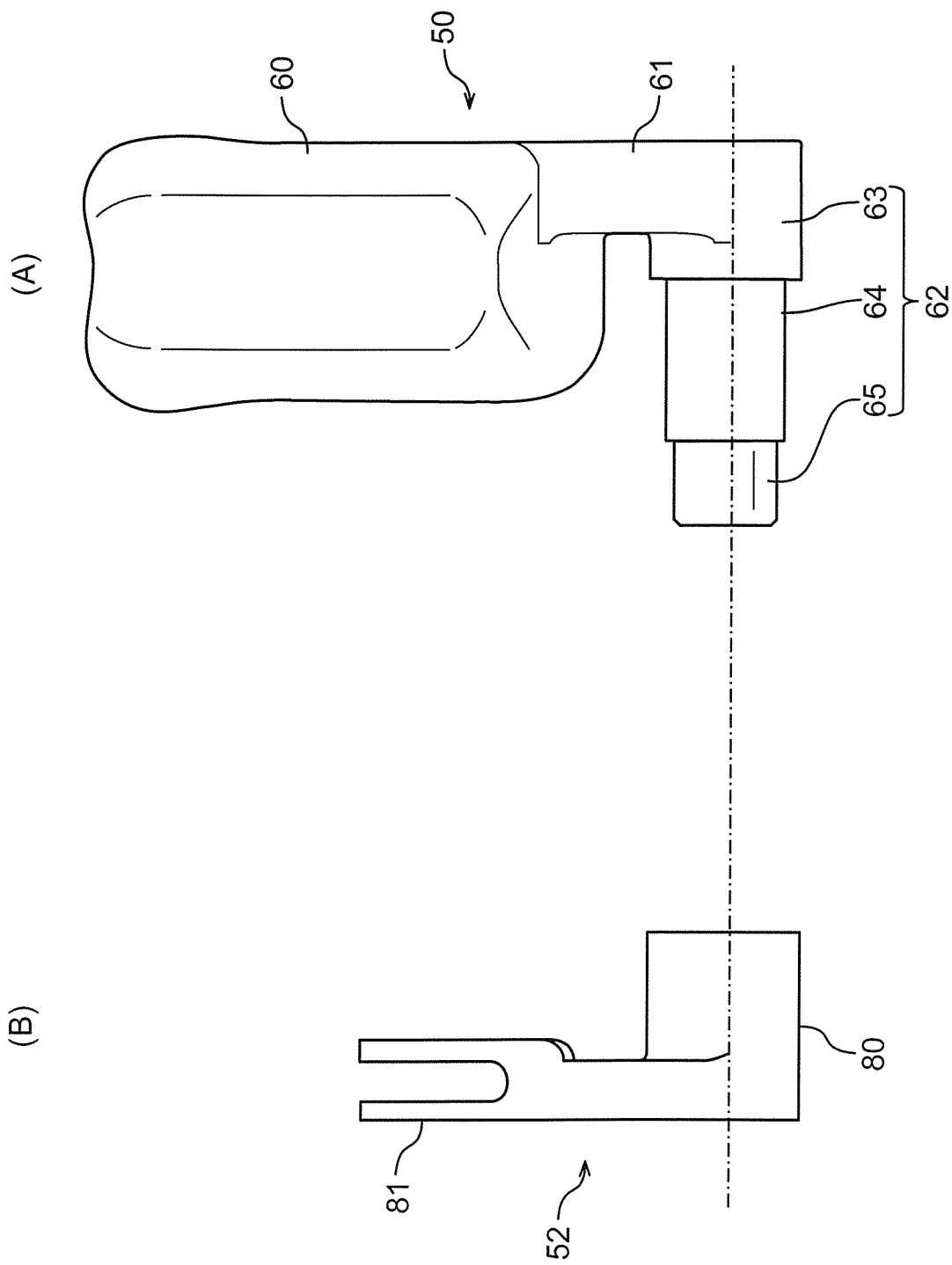
FIG. 10 is a front view of an elevator and an elevation lever of a second embodiment in a coupling mechanism of the second embodiment for coupling the elevator and the elevation lever.
Figure 11:
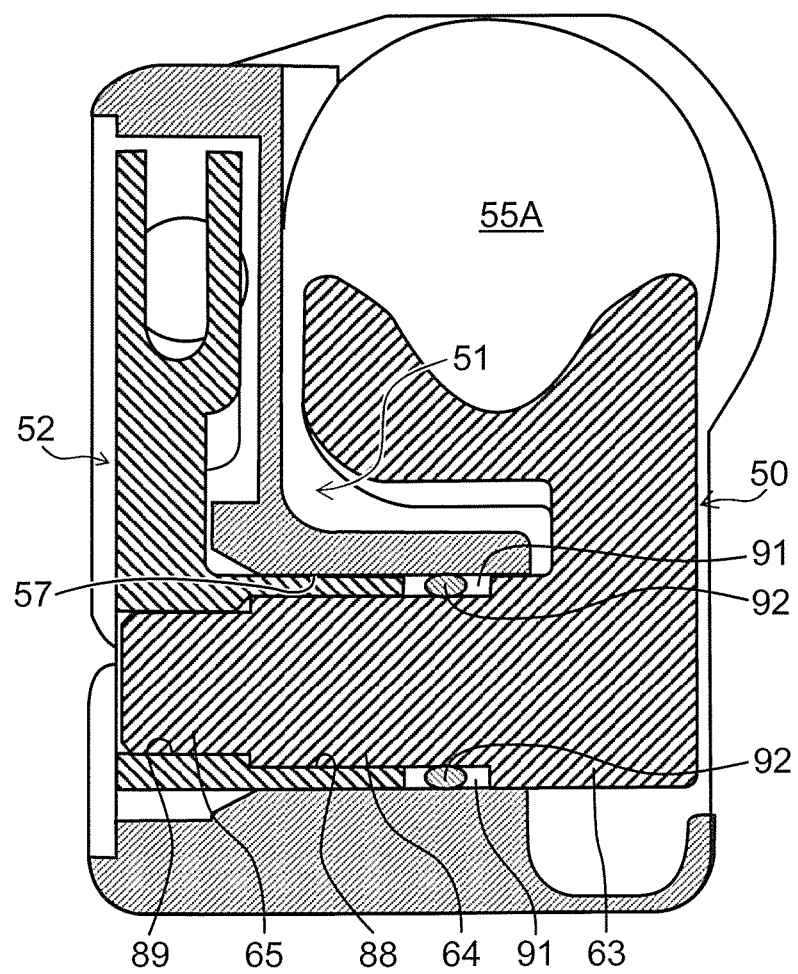
FIG. 11 is a sectional view of the coupling mechanism of the second embodiment in the elevator assembly, taken along a plane including an axis of an elevator rotation shaft portion, the plane being perpendicular to the axis of the insertion section.

FIG. 10 is a front view of the elevator 50 and the elevation lever 52 of the second embodiment in the elevator-lever coupling mechanism of the second embodiment, and FIG. 11 is a sectional view of the elevator-lever coupling mechanism of the second embodiment in the elevator assembly 49, taken along a plane including the axis of the elevator rotation shaft portion 62 (bearing hole 57), the plane being perpendicular to an axis of the leading end section 20 (longitudinal axis of the insertion section 10). A component having a function identical or similar to that of a component of the first embodiment is designated by the same reference numeral so that description on the component is not duplicated.

The elevator-lever coupling mechanism of the second embodiment is configured to couple the elevator rotation shaft portion 62 and the lever rotation shaft portion 80 to each other by fitting without using a screw like the first embodiment.

As illustrated in the (A) portion of FIGS. 10 and 11, the elevator rotation shaft portion 62 of the elevator 50 projects from the support portion 61, and includes a cylindrical large diameter portion 63, a cylindrical small diameter portion 64, and a rotation regulation portion 65 like a quadrangular prism in order from the support portion 61. The small diameter portion 64 is axially longer than the elevator rotation shaft portion 62 of the elevator 50 of the first embodiment.

Meanwhile, as illustrated in the (B) portion of FIGS. 10 and 11, the lever rotation shaft portion 80 of the elevation lever 52 is formed like a column, and has an outer diameter that is substantially equal to the inner diameter of the bearing hole 57 of the assembly body 51.

A cylindrical first fitting hole 88 having an inner diameter substantially equal to an outer diameter of the small diameter portion 64 of the elevator rotation shaft portion 62 is formed in a leading end face of the lever rotation shaft portion 80 toward an opposite face thereof along the axis of the lever rotation shaft portion 80.

The first fitting hole 88 has an axial length less than an axial length of the small diameter portion 64.

A second fitting hole 89 like a quadrangular prism is formed in a bottom face of the first fitting hole 88 toward an opposite face thereof along the axis of the lever rotation shaft portion 80 while penetrating the bottom face so that the rotation regulation portion 65 of the elevator rotation shaft portion 62 can be fitted into the second fitting hole 89 substantially without a gap.

The elevator 50 and the elevation lever 52 in the elevator-lever coupling mechanism of the second embodiment described above allow the elevator rotation shaft portion 62 of the elevator 50 to be inserted from the recessed portion 53B in the assembly body 51 of the elevator assembly 49, and allow the lever rotation shaft portion 80 of the elevation lever 52 to be inserted into the bearing hole 57 from the lever accommodation space 56A opposite to the recessed portion 53B.

Then, the small diameter portion 64 and the rotation regulation portion 65 of the elevator rotation shaft portion 62 are fitted into the first fitting hole 88 and the second fitting hole 89 in the lever rotation shaft portion 80, respectively, to allow the elevator rotation shaft portion 62 and the lever rotation shaft portion 80 to be coupled to each other at a predetermined rotation angle.

As a result, the elevator rotation shaft portion 62 and the lever rotation shaft portion 80 are coupled to each other by fitting.

The elevator rotation shaft portion 62 and the lever rotation shaft portion 80 may be coupled to each other by only press-fitting the rotation regulation portion 65 of the elevator rotation shaft portion 62 into the second fitting hole 89 in the lever rotation shaft portion 80, or may be coupled to each other by allowing the elevator rotation shaft portion 62 and the lever rotation shaft portion 80 to adhere to each other with an adhesive at their contact portion.

In addition, a seal groove 91 along a circumferential direction, as a position regulation groove of the seal member 92, is formed between a first regulation face that is a stepped face formed in a step between the large diameter portion 63 and the small diameter portion 64 of the elevator rotation shaft portion 62, and a second regulation face that is the leading end face of the lever rotation shaft portion 80 and faces the first regulation face. The first regulation face and the second regulation face each have a normal direction that is an axial direction of the elevator rotation shaft portion 62.

Meanwhile, before the elevator rotation shaft portion 62 is inserted into the bearing hole 57 of the assembly body 51, the seal member 92 is fitted around an outer peripheral surface of the small diameter portion 64. Thus, when the elevator rotation shaft portion 62 is inserted into the bearing hole 57 to couple the elevator rotation shaft portion 62 and the lever rotation shaft portion 80 to each other, the seal groove 91 serves as a positioning portion for positioning the seal member 92 in the axial direction of the bearing hole 57 to allow the seal member 92 to be disposed in the seal groove 91 while the seal member 92 is positioned. Then, the seal member 92 is brought into close contact with an internal wall face of the bearing hole 57.

This enables an effect identical to that of the elevator-lever coupling mechanism of the first embodiment to be acquired, as well as the number of components to be reduced as compared with the elevator-lever coupling mechanism of the first embodiment.

While the elevation lever 52 has the lever rotation shaft portion 80 as the second rotation shaft portion in the first and second embodiments of the elevator-lever coupling mechanism, the elevation lever 52 may not have the lever rotation shaft portion 80. In this case, the elevator rotation shaft portion 62 of the elevator 50 is configured to be directly coupled to a body portion (plate-shaped portion) of the elevation lever 52.

In the embodiment described above, while there is described the case where the present invention is applied to the ultrasound endoscope 2 including the ultrasound observation section 100 and the elevator 50 in the leading end section 20, the present invention can be applied to even an endoscope without an ultrasound observation section, such as a side-viewing endoscope including an elevator.

What is claimed is:

1. An endoscope comprising:
an insertion section having a leading end and a base end;
an operation section provided at the base end of the insertion section;
a leading end body provided at the leading end of the insertion section;
an elevator that is provided in the leading end body, and has a first rotation shaft portion formed in a direction including a component of a direction orthogonal to a longitudinal axis of the insertion section, wherein the elevator and the first rotation shaft portion are a one-piece component;
an elevation lever that is provided in the leading end body to allow the elevator to rise and lie, the elevator transferring turning force to the first rotation shaft portion;
an operation wire that is provided from the operation section to the leading end body through the insertion section to transfer displacement generated in the operation section to the elevation lever;
an elevator accommodation section provided in the leading end body,
the elevator accommodation section including:
an elevator accommodation space in which the elevator is accommodated;
a partition wall provided between the elevator and the elevation lever; and
a bearing hole that is provided in the partition wall to support the first rotation shaft portion; and
a seal member provided in the bearing hole,
wherein the elevator accommodation space has an open portion opened toward an opposite side to the partition wall in the elevator accommodation section, and the open portion is formed in an area including the elevator disposed in the elevator accommodation space as viewed from an axial direction of the bearing hole;
wherein the elevation lever includes a second rotation shaft portion that is coupled to the first rotation shaft portion so that a coupled position between the first rotation shaft portion and the second rotation shaft portion is disposed closer to the elevation lever than the seal member, and a seal groove that effects positioning of the seal member in the axial direction of the bearing hole; and wherein the first rotation shaft portion includes a large diameter portion, a small diameter portion that is provided adjacent to the large diameter portion on a side facing the elevation lever, and has an outer diameter less than that of the large diameter portion, a first regulation face that is formed in a step between the large diameter portion and the small diameter portion, and has a normal direction that is in an axial direction of the first rotation shaft portion, the second rotation shaft portion includes a second regulation face that faces the first regulation face when coupled to the first rotation shaft portion, and the seal groove is composed of the first regulation face and the second regulation face.

2. The endoscope according to claim 1, wherein the seal groove is composed of a position regulation groove provided in the first rotation shaft portion or the second rotation shaft portion.

3. The endoscope according to claim 2, wherein the second rotation shaft portion is coupled to the first rotation shaft portion with a screw.

4. The endoscope according to claim 3, wherein the leading end body includes an optical observation section in which an observation window is disposed to acquire an optical image of a subject,
the optical observation section is provided on a side where the open portion of the elevator accommodation section is provided as viewed from the leading end side along the longitudinal axis of the insertion section, and
the optical observation section is provided in an area overlapping with at least the first rotation shaft portion of the elevator as viewed from the axial direction of the bearing hole in a state where the elevator accommodation section and the optical observation section are assembled in the leading end body.

5. The endoscope according to claim 2, wherein the second rotation shaft portion is coupled to the first rotation shaft portion by fitting.

6. The endoscope according to claim 2, wherein the leading end body includes an optical observation section in which an observation window is disposed to acquire an optical image of a subject,
the optical observation section is provided on a side where the open portion of the elevator accommodation section is provided as viewed from the leading end side along the longitudinal axis of the insertion section, and
the optical observation section is provided in an area overlapping with at least the first rotation shaft portion of the elevator as viewed from the axial direction of the bearing hole in a state where the elevator accommodation section and the optical observation section are assembled in the leading end body.

7. The endoscope according to claim 1, wherein the seal groove is composed of a position regulation groove provided in an internal wall face of the bearing hole of the partition wall.

8. The endoscope according to claim 7, wherein the second rotation shaft portion is coupled to the first rotation shaft portion with a screw.

9. The endoscope according to claim 7, wherein the second rotation shaft portion is coupled to the first rotation shaft portion by fitting.

10. The endoscope according to claim 7, wherein the leading end body includes an optical observation section in which an observation window is disposed to acquire an optical image of a subject,
the optical observation section is provided on a side where the open portion of the elevator accommodation section is provided as viewed from the leading end side along the longitudinal axis of the insertion section, and
the optical observation section is provided in an area overlapping with at least the first rotation shaft portion of the elevator as viewed from the axial direction of the bearing hole in a state where the elevator accommodation section and the optical observation section are assembled in the leading end body.

11. The endoscope according to claim 1, wherein the second rotation shaft portion is coupled to the first rotation shaft portion with a screw.

12. The endoscope according to claim 11, wherein the leading end body includes an optical observation section in which an observation window is disposed to acquire an optical image of a subject,
the optical observation section is provided on a side where the open portion of the elevator accommodation section is provided as viewed from the leading end side along the longitudinal axis of the insertion section, and
the optical observation section is provided in an area overlapping with at least the first rotation shaft portion of the elevator as viewed from the axial direction of the bearing hole in a state where the elevator accommodation section and the optical observation section are assembled in the leading end body.

13. The endoscope according to claim 1, wherein the second rotation shaft portion is coupled to the first rotation shaft portion by fitting.

14. The endoscope according to claim 1, wherein the leading end body includes an optical observation section in which an observation window is disposed to acquire an optical image of a subject,
the optical observation section is provided on a side where the open portion of the elevator accommodation section is provided as viewed from the leading end side along the longitudinal axis of the insertion section, and
the optical observation section is provided in an area overlapping with at least the first rotation shaft portion of the elevator as viewed from the axial direction of the bearing hole in a state where the elevator accommodation section and the optical observation section are assembled in the leading end body.

* * * * *